US011684514B2

United States Patent
Fava et al.

(10) Patent No.: US 11,684,514 B2
(45) Date of Patent: Jun. 27, 2023

(54) DIRECT DIODE LASER MODULE FOR DELIVERING PULSED VISIBLE GREEN LASER ENERGY

(71) Applicant: Norlase ApS, Ballerup (DK)

(72) Inventors: Greg Fava, Redwood City, CA (US); Bjarke Goth, Ballerup (DK); Peter Skovgaard, Birkerod (DK)

(73) Assignee: Norlase ApS, Ballerup (DK)

( * ) Notice: Subject to any disclaimer, the term of this patent is extended or adjusted under 35 U.S.C. 154(b) by 209 days.

(21) Appl. No.: 16/584,037

(22) Filed: Sep. 26, 2019

(65) Prior Publication Data

US 2020/0093640 A1    Mar. 26, 2020

Related U.S. Application Data

(60) Provisional application No. 62/736,694, filed on Sep. 26, 2018.

(51) Int. Cl.
*A61F 9/008*    (2006.01)
*H01S 3/0941*    (2006.01)
(Continued)

(52) U.S. Cl.
CPC ........ *A61F 9/00823* (2013.01); *H01S 3/0941* (2013.01); *H01S 3/1312* (2013.01);
(Continued)

(58) Field of Classification Search
CPC . A61F 9/00823; H01S 3/1312; A61N 5/0622; A61N 5/0625; G05B 2219/2617;
(Continued)

(56) References Cited

U.S. PATENT DOCUMENTS 5,757,831 A    5/1998 Kmetec et al.
5,982,789 A    11/1999 Marshall et al.
(Continued)

FOREIGN PATENT DOCUMENTS

DE    103 31 792 A1    2/2005
EP    1 184 948 A2    6/2002
(Continued)

OTHER PUBLICATIONS

Anderson, R.R., et al., "Selective Photothermolysis Precise Microsurgery by Selective Absorption of Pulsed Radiation," Science, 220(4596): 524-527 (1983).
(Continued)

*Primary Examiner* — Tuan N Nguyen
(74) *Attorney, Agent, or Firm* — HoustonHogle LLP

(57) ABSTRACT

A laser module produces pulsed laser energy in a wavelength range of 495-580 nm based on duration, peak power, and interval parameter information. An envelope timer controls the total duration of all micropulses based on the duration and interval parameters via a pulse-width modulated (PWM) output to a micropulse timer, which in turn outputs a PWM micropulse signal. A light emitting diode driver outputs a laser current through a diode based on the micropulse signal and a dimming signal to produce the pulsed laser energy. The integrator compares a signal corresponding to a detected power level of the laser energy to a signal corresponding to the peak power parameter and outputs the dimming signal. The resulting micropulse durations are in the range of 50 to 300 microseconds for periods of about 2 milliseconds, with a duty cycle ranging from 5 to 15%. The overall pulse parameters are duration from 10 microseconds to 1.5 seconds, with periods of any value. The pulsed laser energy is delivered by ophthalmologic laser treatment devices to an eye of a patient.

23 Claims, 15 Drawing Sheets

(51) Int. Cl.
H01S 3/131 (2006.01)
H01S 3/13 (2006.01)
H01S 5/00 (2006.01)

(52) U.S. Cl.
CPC ............... A61F 2009/00844 (2013.01); A61F 2009/00863 (2013.01); G05B 2219/2617 (2013.01); H01S 3/1305 (2013.01); H01S 5/005 (2013.01)

(58) Field of Classification Search
CPC ............ G05B 2219/26; G05B 2219/00; A61B 2017/00203
USPC ........................................................... 606/4
See application file for complete search history.

(56) References Cited

U.S. PATENT DOCUMENTS

| | | | |
|---|---|---|---|
| 6,099,522 | A | 8/2000 | Knopp et al. |
| 6,130,900 | A | 10/2000 | Black et al. |
| 7,771,417 | B2 | 8/2010 | Telfair et al. |
| 2001/0021205 | A1 | 9/2001 | Kittelmann et al. |
| 2003/0078567 | A1 | 4/2003 | Dorin et al. |
| 2004/0036975 | A1* | 2/2004 | Slatkine ................. A61B 90/04 359/584 |
| 2004/0039378 | A1 | 2/2004 | Lin |
| 2004/0098070 | A1 | 5/2004 | Mohr et al. |
| 2004/0116909 | A1* | 6/2004 | Neuberger .......... A61F 9/00821 606/4 |
| 2005/0143720 | A1* | 6/2005 | Yamada ................. A61B 18/20 606/10 |
| 2006/0111697 | A1 | 5/2006 | Brinkmann et al. |
| 2006/0187978 | A1* | 8/2006 | Telfair ................ A61F 9/00821 372/75 |
| 2008/0188838 | A1* | 8/2008 | Abe ........................ A61F 9/008 606/4 |
| 2011/0245816 | A1* | 10/2011 | Abe .................... A61F 9/00821 606/4 |
| 2012/0184857 | A1* | 7/2012 | Yokosuka ........... A61F 9/00821 606/4 |
| 2013/0253411 | A1* | 9/2013 | Rubinchik .......... A61F 9/00821 604/20 |
| 2013/0317570 | A1 | 11/2013 | Luttrull et al. |
| 2014/0128856 | A1* | 5/2014 | Wysopal ............. A61F 9/00825 606/5 |
| 2014/0135750 | A1* | 5/2014 | Hailmann ................ A61F 9/009 606/4 |
| 2014/0257255 | A1* | 9/2014 | Lee ..................... A61B 3/0025 606/4 |
| 2014/0288539 | A1* | 9/2014 | Bischoff ............. A61F 9/00836 606/4 |
| 2015/0366713 | A1* | 12/2015 | Shazly ..................... A61B 3/12 606/5 |
| 2016/0058617 | A1 | 3/2016 | Luttrull et al. |
| 2017/0112572 | A1* | 4/2017 | Shazly ................ A61F 9/00821 |
| 2018/0368915 | A1* | 12/2018 | Xia ..................... A61F 9/00821 |
| 2019/0209372 | A1* | 7/2019 | Farley .................... A61B 3/145 |

FOREIGN PATENT DOCUMENTS

| | | |
|---|---|---|
| EP | 1 856 774 | 8/2016 |
| WO | WO 0180792 | 4/2001 |
| WO | WO 2006091714 | 8/2006 |
| WO | WO-2017167657 A1 * | 10/2017 ......... A61F 9/00814 |
| WO | WO-2018146070 A2 * | 8/2018 ............. A61B 17/00 |

OTHER PUBLICATIONS

Anonymous, "Fovea-Friendly MicroPulse Laser Therapy," Iridex, 1-32 (2015).
Anonymous, "Fox Ophthalmology Laser," A.R.C. Laser, 1-4 (2003).
Anonymous, "TPS92512 2.5A Buck LED Driver with Integrated Analog Current Adjust," 1-30 (2015).
Brinkmann, R., et al., "Laser Induced Shockwave Lithotripsy by Use of an 1µ Alexandrite Laser," Laser Surgery: Advanced Characterization, Therapeutic, and Systems II, 1200, 67-74 (1990).
Brinkmann, R., et al., "Selective RPE-Photodestruction: Mechanism of Cell Damage by Pulsed Laser Irradiance in the ns to µs Time Regime," Part of the SPIE Conference on Laser-Tissue Interaction X: Photochemical, Photothermal, and Photomechanical, 3601, 59-65 (1999).
Byer, R.L., "Diode Laser-Pumped Solid-State Lasers," Science, 239(4841): 742-747 (1988).
Cardillo, J.A., "DME Refractive to 6 Injections of Bevacizumab/IQ 577," (2018).
Cardillo, J.A., "DME Refractive to 7 Injections of Bevacizumab/IQ 577," (2018).
Dorin, G., "Evolution of Retinal Laser Therapy: Minimum Intensity Photocoagulation (MIP). Can the Laser Heal the Retina Without Harming It," Seminars in Ophthamalogy, 19(1-2): 62-68 (2004).
Dorin, G., "Subthreshold and Micropulse Diod Laser Photocoagulation," Seminars in Ophthalmology, 18(3): 147-153 (2003).
Gawecki, M., "Increase in Central Retinal Edema after Subhreshold Diode Micropulse Laser Treatment of Chronic Central Serous Chorioretinopathy," Case Reports i nOphthalmological Medicine, 2015: 1-4 (2015).
Gossage, D., "Diabetic Macular Edema/IG 532," MicroPulse Case Report (2012).
Kracht, D., et al., "Green Q-Switched Microsecond Laser Pulses by Overcoupled Intercavity Second Harmonic Generation," Optics Communications, 231: 319-324 (2004).
Luttrull, J. K., et al., "Long-Term Safety, High Resolution Imaging, and Tissue Temperature Modeling of Subvisible Diode Micropulse Photocoagulation for Retinovascular Macular Edema," Retina, the Journal of Retinal and Vitreous Diseases, X(X): 1-12 (2011).
Mainster, M.A., "Decreasing Retinal Photocoagulation Damage: Principles and Techniques," Seminars in Ophthalmology, 14(4): 200-209 (1999).
Mainster, MA., "Wavelength Selection in Macular Photocoagulation," Ophthalmology, 93(7): 952-958 (1986).
Mansour, S.E., "MicroPulse Laser Therapy of Diabetic Macular Edema Success in Anti-VEGF Non-Responder," Iridex, 1-2 (2018).
Moorman, C.M., et al., "Clinical Applications of the MicroPulse Diode Laser," Eye, 13: 145-150 (1999).
Pankratov, M.M., "Pulsed Delivery of Laser Energy in Experimental Thermal Retinal Photocoagulation," Laser-Tissue Interaction, 1202: 205-213 (1990).
Roider, J., et al., "Microphotocoagulation: Selective Effects of Repetitive Short Laser Pulses," Proc. Natl. Acad. Sci USA, 90:8643-8647 (1993).
Schuele, G., et al., "RPE Damage Thresholds and Mechanisms for Laser Exposure in the Microsecond-to-Millisecond Time Regimen," Investigative Ophthalmology & Visual Science, 46(2): 714-719 (2005).
Tang, J., "TxCell-Guided Micropulse Laser Therapy Increases Treatment Efficiency for Diabetic Macular Edema," Iridex (2014).
Vogel, A., et al., "Temperature Profiles in Human Retina and Choroid Laser Coagulation with Different Wavelengths Ranging from 514 to 810 nm," Lasers and Light Ophthalmology, 5(1): 9-16 (1992).
Yu, A.K., et al., "The Comparative Histologic Effects of Subthreshold 532- and 810-nm Diod Micropulse Laser on the Retina," Investigative Opthamology & Visual Science, 54(3): 2216-2224 (2013).
Sutter, E., "Protection from Optical Radiation," Schutz vor optischer Strahlung 2. Auflage, 2002, VDE Verlag Berlin, Offenbach (2002).
Anonymous, "EN 60601-2-22:1996 Medical Electrical Equipment—Particular Requirements for the Safety of Diagnostic and Therapeutic Laser Equipment," Norm fUr medizinischer Laser: EN 60601-2-22:1996, Seite 9, 11Hauptabschnitt acht-Genauigkeit der Betriebsdaten und Schutz gegen gefahrdende Ausgangswerte, Unterabschnitt 51"Schutz gegen gefahrdende Ausgangswerte" (1996).

* cited by examiner

DIRECT DIODE LASER MODULE FOR DELIVERING PULSED VISIBLE GREEN LASER ENERGY

RELATED APPLICATIONS

This application claims the benefit under 35 USC 119(e) of U.S. Provisional Application No. 62/736,694, filed on Sep. 26, 2018, which is incorporated herein by reference in its entirety.

BACKGROUND OF THE INVENTION

There are a number of treatment regimes that involve delivering laser energy to the patient's eye. In these treatments, doctors regularly set and update parameters for the laser energy to be delivered. These parameters can include peak power, duration, and repeat interval, among other examples. Many of the treatments involve delivering laser energy in a wavelength range of 495-580 nanometers (nm) associated with visible green and yellow light. The treatments also require sufficiently high output powers so as to allow the structures of the eye to absorb sufficient energy at a selected, well-defined target site within short period of times.

Commonly, slit lamps are used for delivering the laser energy to the patient's eye. In these systems, the patients sit up in an examination chair, rest their chin on a chin rest, and place their forehead against a forehead band, both of which keep the patient's head in place during the procedure.

Another common device is a Laser Indirect Ophthalmoscope (LIO), which is a head mounted device, worn by the doctor to deliver laser energy into a patient's eye. Current systems use a laser console for generating the laser light and a long fiber optic coupled to the LIO. The laser console includes a laser source, a power source (for example, providing AC/DC conversion), laser drive and parameter control systems, and a user interface. The user interface comprises physical knobs and switches or a touchscreen and can be part of the laser console itself or a remote control device that communicates with the laser console. Activation devices (e.g. footswitches) connect to the laser consoles and activate the laser emission, for example, by sending an activation signal to the laser console in response to engagement of an activation mechanism (e.g. compression of the footswitch).

During procedures using the LIO, the doctor moves the laser console, which is positioned on a cart or table, to be in the proximity of the patient who is usually in a supine position. The doctor then walks around the patient to deliver the laser energy to the desired portions of the retina. If a parameter change is needed, the doctor physically returns to the laser console to make the change or has an assistant, for example, standing next to the laser console, make the change.

In other ophthalmic laser treatment systems, photocoagulation laser probes are used in place of the LIO to deliver the laser energy. Here, the probes, which are handheld wands or pens of varying sizes, are connected to the laser console via a fiber optic cable. The laser console produces the laser light, which is then directed through the laser probe and emitted from the tip of the probe to the patient's eye.

Many of these treatments involve delivering the laser energy in a pulse train consisting of discrete pulses known as micropulses, which limit the amount of damage at the target tissue and spare adjacent tissues from any thermal injury. The characteristics of the pulse trains, which vary based on different types of treatments, are based on overall pulse parameters such as pulse train duration, interval and peak power, along with micropulse parameters such as micropulse duration and micropulse interval. The micropulse duration represents the time during which the laser energy is delivered during each micropulse, the micropulse interval represents the time after each micropulse and before the next pulse, during which no laser energy is delivered. Typically, the micropulses are repeated at evenly spaced intervals across the envelope, or pulse train duration. The micropulse period represents the total combined time for each micropulse and its succeeding interval. A proportion of the micropulse duration to the micropulse period is referred to as the duty cycle.

One system for delivering pulsed laser energy in the visible range to a patient's eye is described in U.S. Pat. No. 7,771,417 B2 to Telfair et al (hereinafter referred to as "Telfair"). In Telfair, a frequency doubled solid state visible laser is pumped by a diode pump source and produces pulsed laser output for use in ophthalmologic treatments in the wavelength range 520 to 615 nm.

SUMMARY OF THE INVENTION

A need exists for more portable and efficient systems for delivering pulsed laser energy to the eye of a patient in ophthalmologic treatments. At the same time, higher power diode lasers are currently in development. In one example, the lasers produce laser energy in the visible green range with an output power of 1 Watt, and similar green diode lasers with even higher output powers are anticipated as the technology continues to mature. In this vein, these higher-power direct diode lasers can be used to deliver the pulsed laser energy, decreasing the size, complexity and cost of the laser module and at the same time increasing its efficiency.

The present invention concerns a laser module for delivering pulsed laser energy in the visible green wavelength range for ophthalmologic treatments. The laser module electronically pulses a laser diode in the millisecond range to microsecond range based on duration, peak power, and interval parameter information received via a user interface.

More specifically, a user interface receives input from a user indicating a pulse duration, interval and peak power, and a micropulse duration and interval and generates parameter information based on the input.

An envelope timer controls the total duration of all of the micropulses based on the duration and interval parameters via a pulse-width modulated (PWM) output to a micropulse timer clocked at a higher frequency, which in turn drives diodes to produce the pulsed laser energy by modulating an output voltage, for example, by outputting a PWM signal, which is a binary pulse train of high and low voltage states corresponding to the micropulses.

A light emitting diode (LED) driver, operating as a buck converter at a programmable frequency between 0.3 to 2 MHz, converts a 24 V power supply, for example, to a laser or light emitting diode (LED) current based on the modulated voltage from the micropulse timer and dimming input from an integrator. A portion of the laser energy produced is input into a power monitor, which sends a signal to the integrator corresponding to the measured power of the laser energy. The integrator compares the signal corresponding to the power of the laser energy to a signal from the controller corresponding to the peak power setpoint based on the parameter information.

The resulting micropulse durations are in the range of 50 to 300 microseconds for periods of about 2 milliseconds, with an adjustable duty cycle ranging from 5 to 15%, or as high as 90%. The overall pulse parameters are duration from 10 milliseconds to 1.5 seconds, with periods of any value.

In general, according to one aspect, the invention features a laser module for producing pulsed laser energy for an ophthalmic laser treatment system. One or more diodes of the laser module produce the pulsed laser energy in a visible green wavelength range, and a controller drives the diodes based on parameter information.

In embodiments, durations of discrete pulses of the pulsed laser energy are in a range of 50 to 300 microseconds, the diodes are configured to produce laser energy with an output power of 1 Watt, and the visible green wavelength range includes wavelengths from 495 to 580 nanometers.

The parameter information includes pulse envelope duration, peak power, interval, pulse duration and pulse interval and is based on input received from a user via a user interface of the ophthalmic laser treatment system.

The laser module further comprises an LED driver for producing an LED current based on a modulated voltage output from the controller based on the parameter information. In this case, the diodes produce the pulsed laser energy based on the LED current from the LED driver.

The laser module further comprises an integrator for adjusting power of the laser energy based on a comparison of detected power of the laser energy to a predetermined peak power set point based on the parameter information. A power monitor of the laser module measures the power of the laser energy and outputs a signal corresponding to the measured power to the integrator to be compared to a signal corresponding to the peak power set point.

In examples, the ophthalmic laser treatment system is a body-mounted and/or table-top laser indirect ophthalmoscope system, a slit-lamp system, or a photocoagulation laser probe system.

In general, according to another aspect, the invention features a method for producing pulsed laser energy for an ophthalmic laser treatment system. Parameter information is received, and one or more diodes produce the pulsed laser energy in a visible green wavelength range based on the parameter information.

In general, according to another aspect, the invention features a system for delivering pulsed laser energy to an eye of a patient. The system comprises a control module and a laser module. The control module for sets parameters for the delivered pulsed laser energy based on received parameter information and sends control signals based on the parameters. The laser module delivers the pulsed laser energy based on the control signals via one or more diodes for producing the pulsed laser energy in a visible green wavelength range.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

The present invention concerns a system for producing pulsed laser energy in the visible green wavelength range for ophthalmologic treatments, which can be embodied in different devices. In general, FIGS. 1-5 concern exemplary systems for delivering the pulsed laser energy to a patient's eye to which the present invention is applicable.

Figure 1:
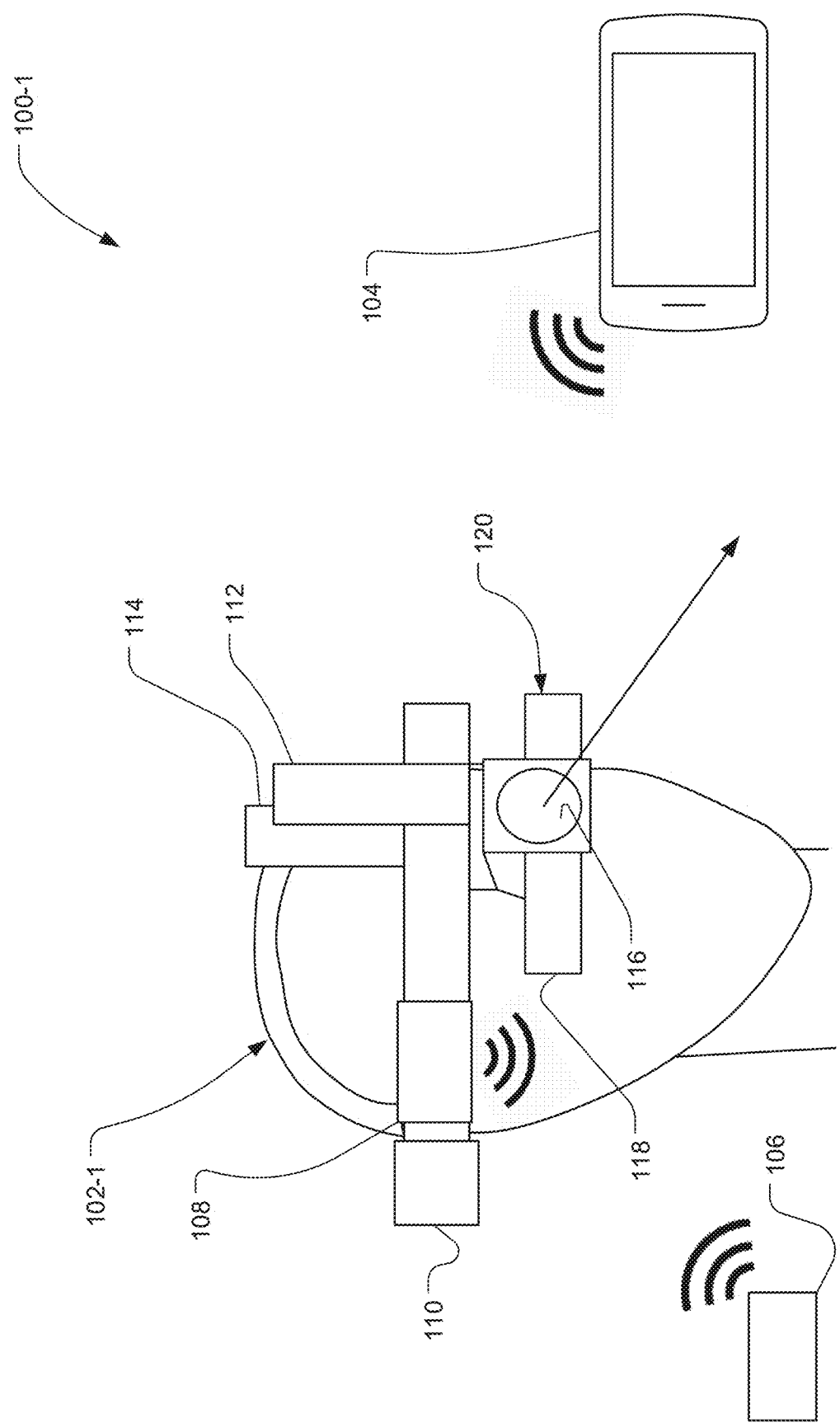
FIG. 1 is an illustration of an exemplary body-mounted laser-indirect ophthalmoscope (LIO) system to which the present invention is applicable.

FIG. 1 is an illustration of a body-mounted LIO system 100. In general, the body-mounted LIO system 100 delivers laser energy to an eye of a patient. A user of the LIO system 100 is typically a doctor such as an ophthalmologist.

The body-mounted LIO system 100 includes a binocular indirect ophthalmoscope 120, a control module 108, a power module 110, a laser module 112 and a mobile computing device 104.

The binocular indirect ophthalmoscope 120 is an optical device for examining the inside of the eye of the patient. The binocular indirect ophthalmoscope 120 includes an illumination unit 114 for providing white light and an optical system including a viewing aperture 118 and an exit aperture 116 from which the laser energy is emitted (which is also an entrance aperture for image information e.g. for viewing the patient's eye).

In general, the power module 110 provides power to the control module 108 and the laser module 112. In one embodiment, the power module 110 also provides power to the illumination unit 114 of the binocular indirect ophthalmoscope 120.

The laser module 112 produces and emits the pulsed laser energy according to certain user-provided parameters such as pulse envelope duration, peak power, and interval, and micropulse duration and interval, among other examples.

The activation device 106 is a device that receives user input via an activation mechanism (e.g. a switch or button) and in response sends activation signals to the control module 108 indicating that the laser energy should be emitted. In the preferred embodiment, the activation device 106 is a footswitch, and engagement with the activation mechanism includes compression of the footswitch by the user's foot, for example.

Preferably, the mobile computing device 120 is a tablet computer. Alternatively, the mobile computing device 120 could be a smartphone device, laptop computer, or phablet computer (i.e., a mobile device that is typically larger than a smart phone, but smaller than a tablet), to list a few examples. In general, the mobile computing device 104 provides a user interface and generates parameter information indicating the user-provided parameters based on input received via the user interface and sends the parameter information to the control module 108. In the illustrated example, the user interface is a voice control interface that allows the user to indicate parameter information using verbal commands. In the illustrated example, the user provides a verbal command ("Power 200"), and the mobile computing device provides audible feedback confirming the command.

The control module 108 controls the laser energy delivered by the laser module 112 based on parameter information received from the mobile computing device 104 and activation signals received from the activation device 106. In the illustrated example, the control module 108 communicates with the activation device 106 and the mobile computing device 104 wirelessly. In response to receiving the parameter information from the mobile computing device 104, the control module 108 sets the parameters for the laser energy. In response to receiving activation signals from the activation device 106, the control module 108 sends control signals reflecting the user-provided parameters to the laser module 112 activating the laser module and causing it to produce and/or emit the laser energy.

The body-mounted LIO system 100 includes a wearable assembly 102, which secures the body-mounted LIO system 100 to the user's body via one or more wearable objects such as a headset, a utility belt, or a backpack, among other examples. In the illustrated example, the wearable assembly 102 comprises only a headset 102-1, which is worn on the user's head.

Figure 2:
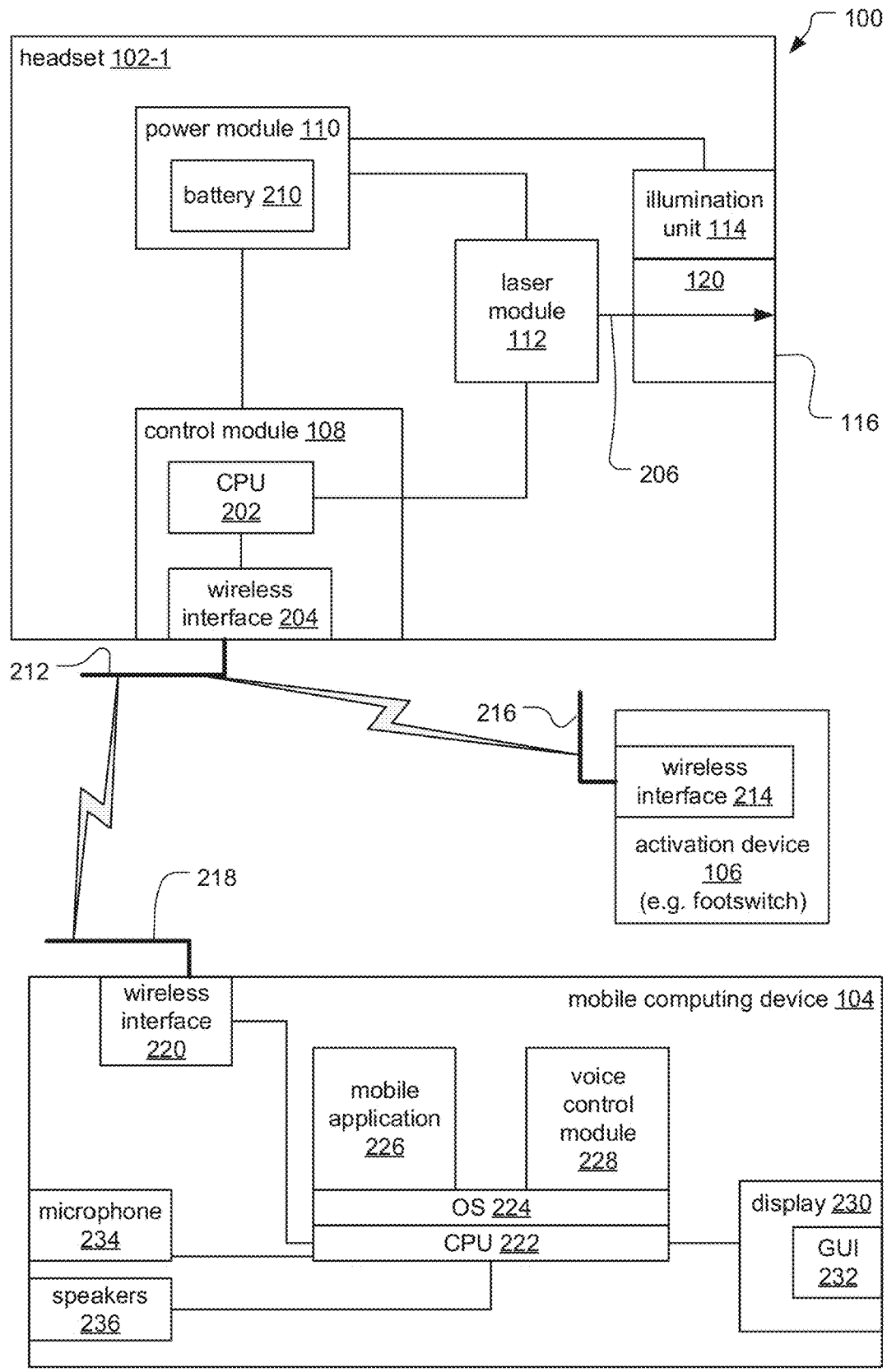
FIG. 2 is a schematic diagram of the body-mounted LIO system to which the present invention is also applicable.

FIG. 2 is a schematic diagram of the body-mounted LIO system 100 according to the preferred embodiment showing the components of the system in more detail. Specifically, internal components of the headset 102-1, the activation device 106, and the mobile computing device 104 are shown.

The mobile computing device 104 includes a CPU 222, a touchscreen display 230, a wireless interface 222 and antenna 218, a microphone 234 and speakers 236.

The CPU 222 executes firmware/operating system instructions and sends instructions and data to and receives data from the wireless interface 220, the microphone 234, the speakers 236, and the display 230. Executing on typically an operating system (OS) 224 of the CPU 222 are a mobile application 226, and a voice control module 228. The mobile application 226 renders a graphical user interface (GUI) 232 on the touchscreen display 230. The GUI 232 displays and receives information such as parameter information, for example, by detecting contact between the user and the touchscreen display 230 in certain regions of the touchscreen display 230. The mobile application 226 also performs functions related to configuring the LIO system 100 such as pairing the mobile computing device 104 with the control module 108 and/or setting a wake word, which is a selected phrase for indicating that verbal commands follow.

The microphone 234 captures sound including the wake word and voice commands indicating parameter information provided by the user, which the mobile computing device 104 converts to audio data.

The voice control module 228 generates parameter information based on the captured audio data. In one example, the voice control module 228 recognizes spoken language in the audio data and translates the spoken language to parameter information.

The speakers 236 provide audible feedback confirming the parameter information by producing sound indicating the parameter information generated by the voice control module 228 based on the audio data.

In the illustrated example, the voice control module 228 and the GUI 232 rendered on the touchscreen display 230 provide a general user interface (UI) for the LIO system 100. However, in other embodiments (not illustrated) the UI for the LIO system 100 can also include physical input mechanisms such as knobs or buttons, which can be part of the mobile computing device 104 itself or part of peripheral devices connected to the mobile computing device 104 via the wireless interface 220 and/or a physical interface (e.g. data port). In general, the parameter information can be generated by the mobile computing device 104 based on any user engagement with the mobile computing device 104 and/or peripheral devices.

The wireless network interface 220 facilitates sending the parameter information to the control module 108 via the antenna 218 through a wireless communication link with the control module 108 according to wireless personal area network (WPAN) or wireless local area network (WLAN) protocols such as Bluetooth Low Energy (BLE) or WiFi, among other examples.

The headset 102-1, as previously discussed, includes the control module 108, the power module 110, the laser module 112, the binocular indirect ophthalmoscope 120 and the illumination unit 114.

The power module 110 includes a battery 210, which supplies the power provided to the control module 108, laser module 112 and illumination unit 114. Among other functions, the power module 110 performs the functions of a battery management system (e.g. preventing the battery from operating outside its Safe Operating Area, monitoring its state, etc.).

The laser module 112 includes a fiber optic cable 206 for emitting the laser energy. The fiber optic cable 206 is routed through the binocular indirect ophthalmoscope 120 such that the laser energy is emitted from the exit aperture 116.

The control module 108 includes a CPU 202 and a wireless interface 204. The CPU 202 directs the functionality of the control module 108 such as receiving parameter information from the mobile computing device 104 and activation signals from the activation device 106 via the wireless interface 204 and an antenna 212, as well as sending control signals to the laser module 112.

Finally, the activation device 106 includes a wireless interface 214 and an antenna 216 through which activation signals are sent to the control module 108.

Figure 3:
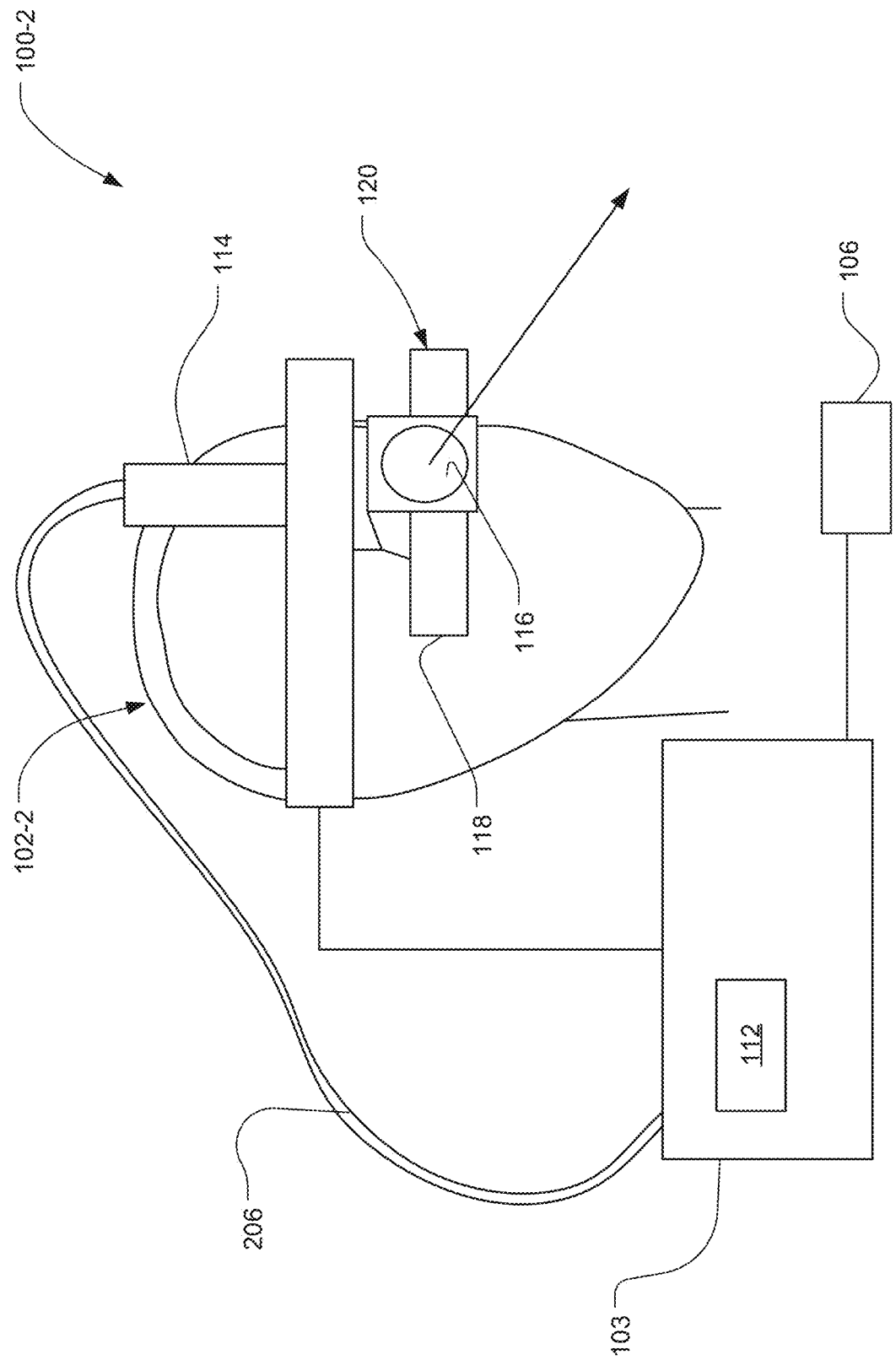
FIG. 3 is an illustration of an exemplary table-top LIO system to which the present invention is also applicable.

FIG. 3 is an illustration of a table-top LIO system 100-2 to which the present invention is applicable.

The table-top LIO system 100-2 includes a laser console 103 and a headset 102-2. The headset 102-2 includes the binocular indirect ophthalmoscope 120 and the illumination unit 114 as before. Now, however, the laser console 103 receives the user input via a user interface of the laser console 103, generates the parameter information, and drives the laser via a longer fiber optic cable 206 which is routed from a laser module 112 housed within the laser console 103 to the headset 102-2. The laser console 103 receives input from the activation device 106 via a wired connection.

Figure 4:
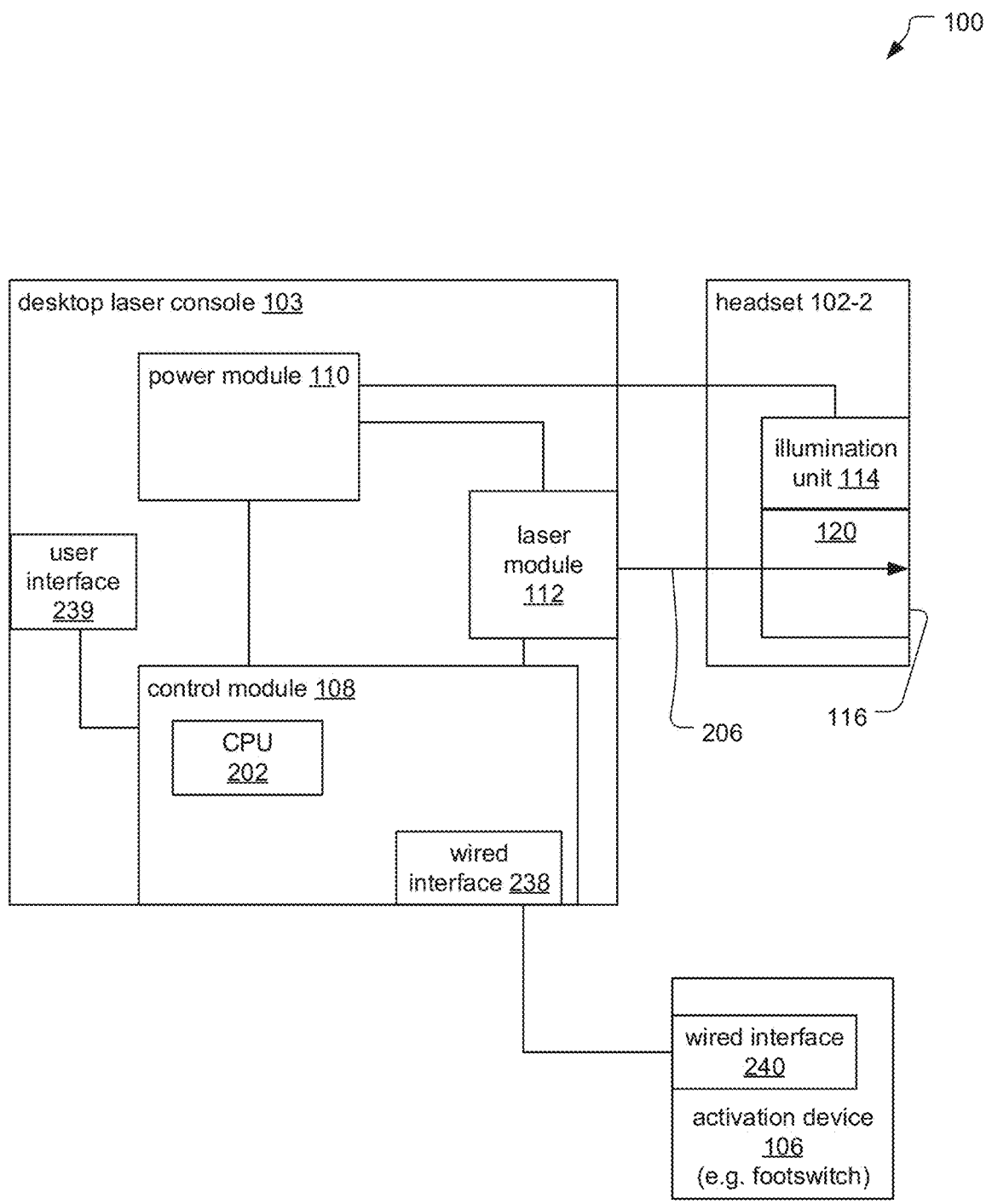
FIG. 4 is a schematic diagram of the table-top LIO system to which the present invention is also applicable.

FIG. 4 is a schematic diagram of the table-top LIO system 100-2. Here, the laser console 103 includes the control module 108, the power module 110, the laser module 112, and a user interface 239, which can include a graphical user interface, or other input and display elements such as knobs, dials, keypads and/or buttons. Additionally, the activation device 106 includes a wired interface 240, and likewise the control module 108 includes a wired interface 238. Instead of sending the activation signals wirelessly to the control module 108, the activation device 106 sends the signals via a wired connection between the two devices.

Figure 5:
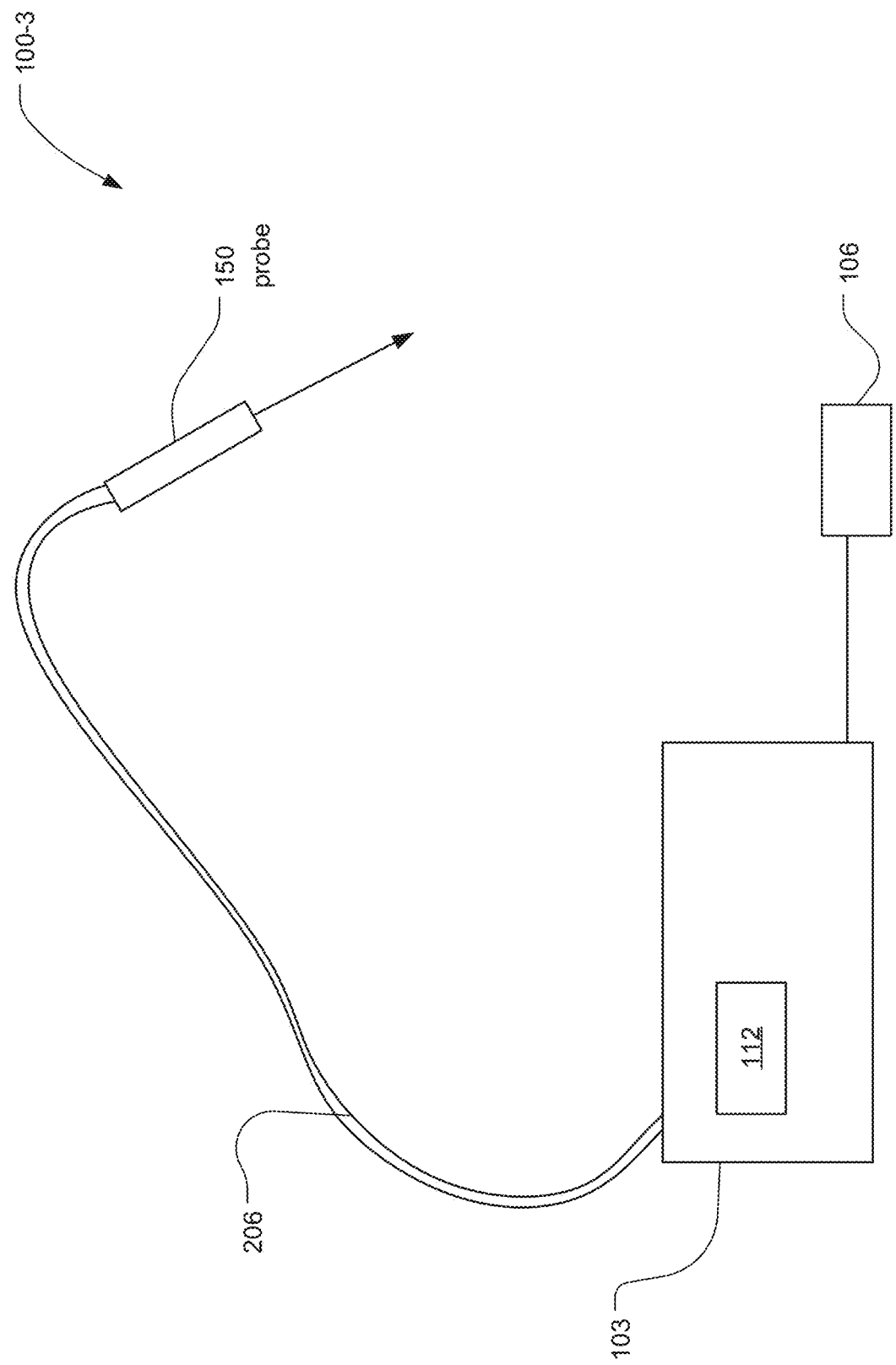
FIG. 5 is an illustration of an exemplary photocoagulation probe laser treatment system to which the present invention is applicable.

FIG. 5 is an illustration of an exemplary photocoagulation probe laser treatment system 100-3 to which the present invention is applicable. The system includes the laser console 103 wired to an activation device 106 as in the table-top LIO system 100-2. Now, however, a photocoagulation probe 150 is connected to the laser console 103 via the fiber optic cable 206. The photocoagulation probe 150 is pen- or wand-shaped, with the fiber optic cable 206 connected to a proximal end of the probe 150 and an exit aperture at a distal end of the probe 150. As before, the laser console 103 produces the laser energy (e.g. via the laser module 112), which is then directed through the probe 150 via the fiber optic cable and is emitted from the distal end of the probe 150 to, for example, the patient's eye.

Figure 6:
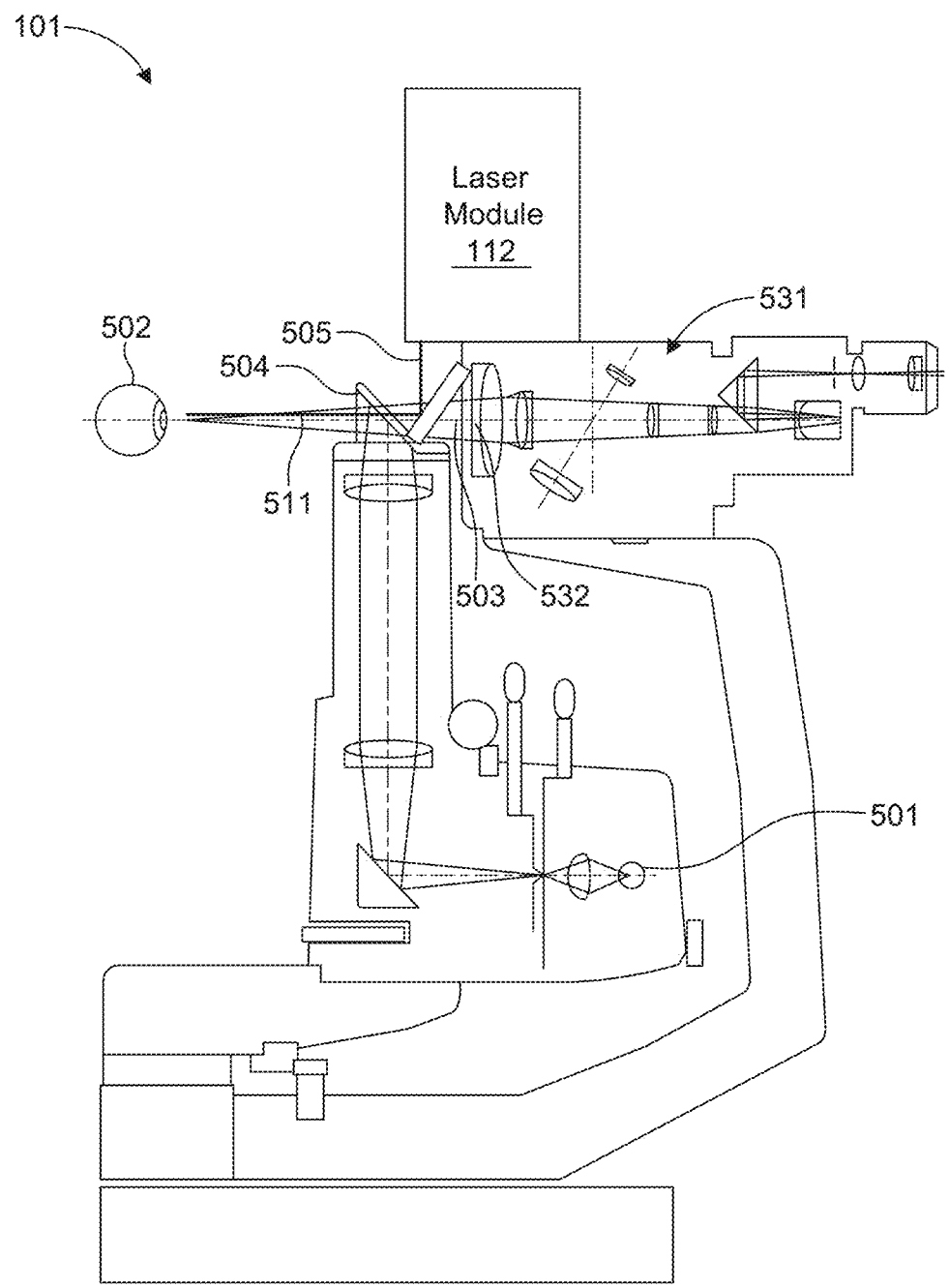
FIG. 6 is an illustration of an exemplary slit lamp system to which the present invention is also applicable.

FIG. 6 schematically shows a slit lamp device 101 to which the present invention is applicable. The figure schematically shows the previously described laser module 112 that produces the pulsed laser energy and that is attached to the slit lamp 101, for example, via a tonometer mount. The slit lamp includes a magnifying optical device 531, such as a microscope or zoom telescope, configured to receive light at a viewing input 532 along a viewing path 503 from a target area. The central part of the slit lamp 101 includes a white light source 501 that is used to illuminate a target area in the eye 502 of the patient. This white light is directed, by means of a mirror 504, onto an illumination output path 511 that coincides with the optical viewing path 503 of the operator at the designed focal point of the diagnostic instrument at the target area. In the same fashion, the light 505 from the laser is directed towards the target area along a treatment beam path such that it coincides with the viewing path, at least at the target area.

Figure 7:
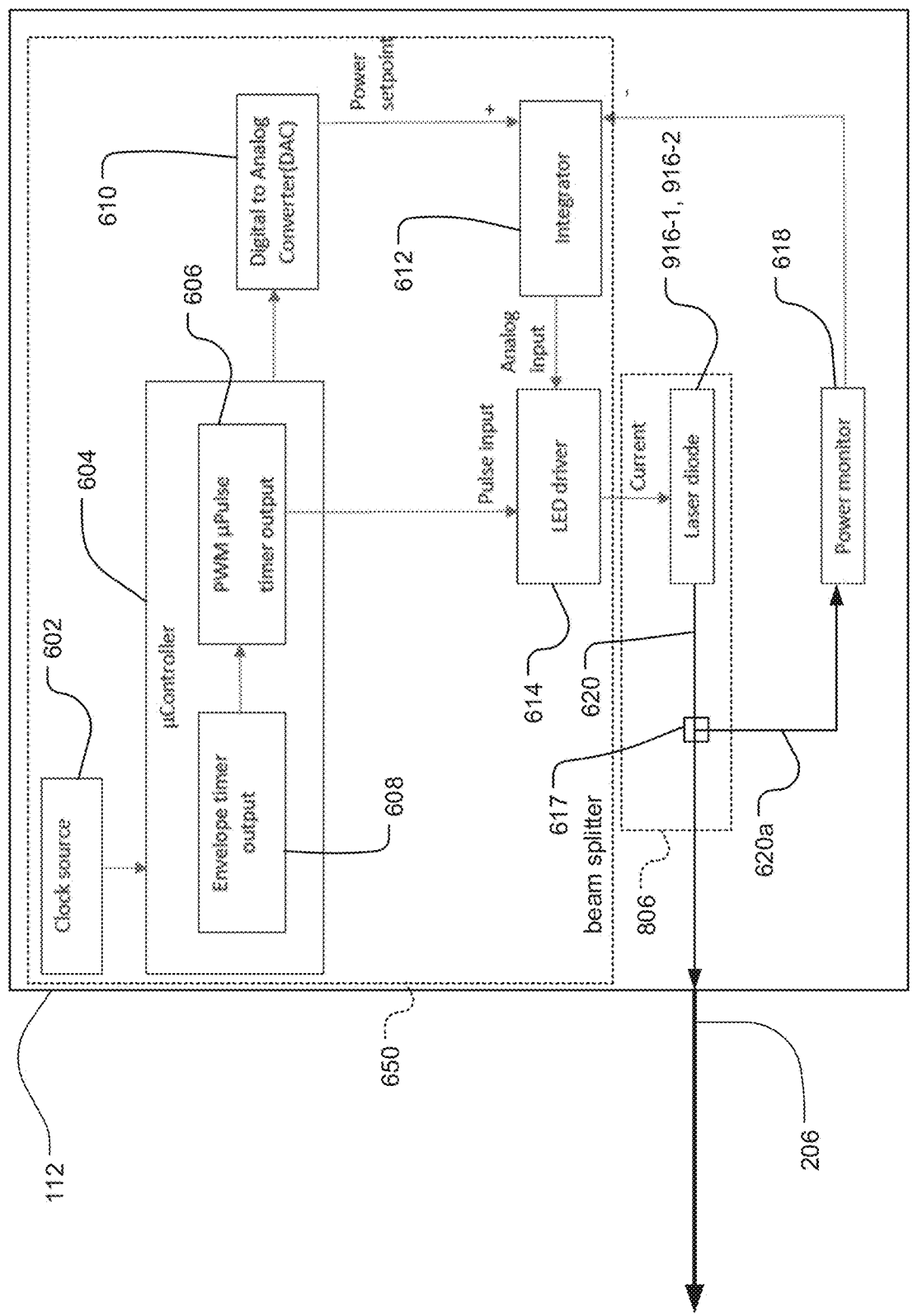
FIG. 7 is a schematic diagram of a laser module according to the present invention.

FIG. 7 is a schematic diagram of the laser module 112 according to an embodiment of the present invention. The laser module 112 generally includes a control circuit board 650 and an optical package 806.

The control circuit board 650 includes electrical components for controlling the laser module 112, including a clock source 602, a microcontroller 604, a digital-to-analog converter 610, a light-emitting diode (LED) driver 614 and an integrator 612.

The optical package 806 is a hermetically sealed to define a chamber containing optical components of the laser module 112, including one or more laser diode(s) 916-1, 916-2.

In general, the laser module 112 is configured to produce pulsed laser energy in a wavelength range of 495-570 nm associated with visible green light.

In operation, a user interface (e.g. the GUI 232 or laser console user interface 239 of the LIO system 100) receives input from a user indicating a pulse duration, interval and peak power, and a micropulse duration and interval and parameter information is generated based on the input.

In general, the microcontroller 604 drives the diodes 916 to produce the pulsed laser energy based on parameter information. For example, the microcontroller 604 receives the parameter information indicating the pulse envelope duration, peak power, and interval and the micropulse duration and interval and modulates an output voltage based on the parameter information, for example, by generating modulated output signals or pulse-width modulated (PWM) signals for producing the pulsed laser energy. In one embodiment, the modulated output voltage includes binary pulse trains corresponding to the desired micropulses to be output by the laser module 112. The modulated output voltage from the microcontroller 604, for example, include binary signals in which the voltage is high or low at different times, with the high voltage corresponding to periods of time during which laser energy should be emitted by the laser module 112 and low voltage corresponding to periods of time during which no laser energy should be emitted by the laser module 112.

More specifically, the microcontroller 604 includes an envelope timer 608 and a micropulse timer 606.

The envelope timer 608 controls the total duration of all of the micropulse periods based on the duration and interval parameters via a PWM output to the micropulse timer 606, which is clocked at a higher frequency. The micropulse timer 606 outputs the PWM signal corresponding to the micropulses to the LED driver 614 by modulating the output voltage from the microcontroller 604 to the LED driver 614.

The microcontroller 604 also outputs a digital value corresponding to the peak power parameter to the digital to analog converter 610, which converts the value to an analog power setpoint signal corresponding to the peak power setting and outputs the power setpoint signal to the integrator 612.

The LED driver 614 interfaces with the microcontroller 614 and the integrator 612 and outputs a laser current to the one or more laser diode(s) 916-1, 916-2 based on the modulated voltage from the micropulse timer 606 and an additional dimming signal from the integrator 612, by down converting a 24 V (for example) DC power supply. In one embodiment, the LED driver 614 operates as a buck converter at a programmable frequency between 0.3 to 2 MHz.

In one embodiment, the LED driver 614 is a chip described in "TPS92512 2.5A Buck LED Driver with Integrated Analog Current Adjust," Texas Instruments, February, 2015 such as a 2.5 A step-down current regulator with an integrated MOSFET for driving high current LEDs with a 4.5V to 42V input voltage range and an output current of up to 2.5 A.

The laser current flows through a junction of the one or more laser diode(s) 916-1, 916-2 producing the laser beam 620, which is pulsed according to the output laser current from the LED driver 614. The laser beam 620 is directed through a beam splitter 617, which splits off a portion 620a of the laser beam 620, which is directed to a power monitor 618, which generates a measured power signal corresponding to the detected power of the laser energy 620 and outputs the measured power signal to the integrator 612.

In one embodiment, the green laser diodes 916 are each configured to produce laser energy in the therapeutic visible green range (e.g. 495-580 nm) with an output power of approximately 1-1.3 Watts.

The integrator 612 compares the measured power signal corresponding to the power of the laser energy 620 from the power monitor 618 to the power setpoint signal corresponding to the peak power parameter and outputs a dimming signal to the LED driver 614, which is used to adjust the laser current to maintain a stable peak power. A dimming input of the LED driver 614 receives the dimming signal from the integrator 612 and controls an enable/disable state of an internal gate driver of the LED driver 614. When the dimming input is low, the gate driver is disabled, and the LED current reduces to zero. The average output current from the LED driver 604 is based on the duty cycle of the dimming signal.

Figure 8:
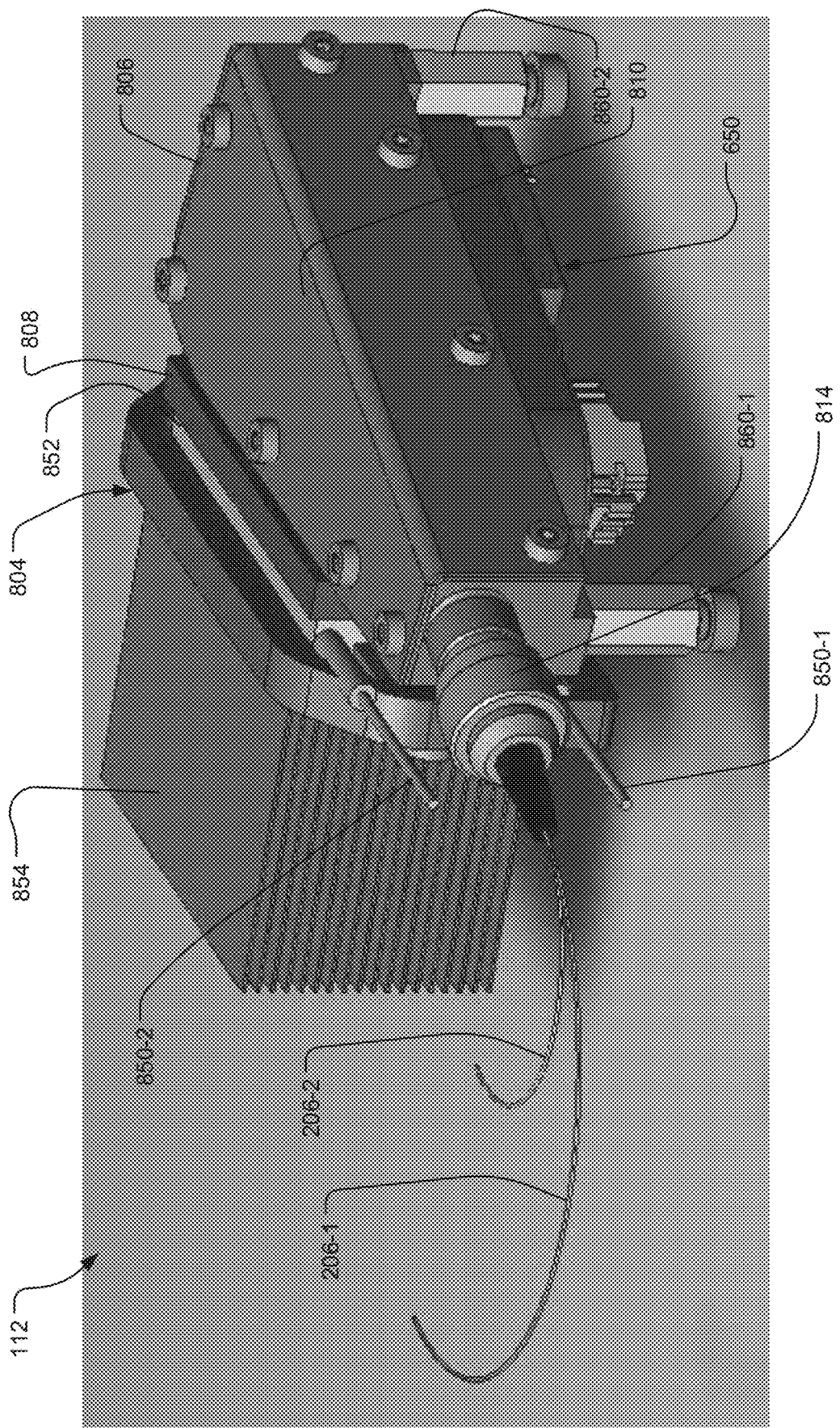
FIG. 8 is a perspective view of the laser module.

FIG. 8 is a perspective view of the laser module 112. In the illustrated example, the laser module 112 includes the hermetically sealed optical package 806 with its lid 810, a heat sink 808, a fiber optic connecter 814, and a thermoelectric cooler unit 804.

The package 806 provides an enclosure for some or all of the components of the laser module 112, which is designed to have an optimal size, shape and weight based on the application of the pulsing direct diode laser module 112. The compactness of size of the package 806 is enabled by the use of the green direct diode lasers 916, instead of solid state lasers, for example.

The power monitor 618 in the illustrated embodiment is not housed within the package 806, but rather external to the package 806 (e.g. in a module that controls the spot size of the delivered laser energy). In this case, an additional fiber optic cable 206-2 directs the split off portion of the laser beam 620a to the power monitor 618.

The package's lid 810 is secured over a top and side surface of the package 806, enclosing and hermetically sealing optical components of the laser module 112 such as the diodes, combiners, and optical components. The fiber optic connecter 814 connects to a male connector on a front surface of the package and directs the emitted laser energy through the fiber optic cable 206.

The wrap-around copper heat sink 808, contacts a side and bottom surface of the laser package 806 opposite the lid 810 and transfers heat generated by the laser diodes in the package 806 to the thermoelectric cooler unit 804, which is secured to the side exterior surface of the heat sink 808.

The thermoelectric cooler unit 804 comprises a cooling plate 852 and a heat sink 854. The cooling plate 852 comprises two electric connectors 850 connected to a series of thermocouples, which are complementarily paired p-type and n-type semiconductor elements, between two dielectric (e.g. ceramic) plates. An electric current moves through the thermocouples via the connectors 850, causing one side of the cooling plate 852 to be cooled and the other to be heated. The heat sink 808, which is in contact with the cooled side of the cooling plate 852, transfers heat from the package 806 to the cooled side. The heat sink 854, which is in contact with the heated side of the cooling plate 852, dissipates heat from the heated side, for example, into the surrounding environment. In this way, the heat sink 808 and thermoelectric cooler unit 804 cool the package 806 by directing heat generated by the diodes in the package 806 away from the package 806.

In one example, the microcontroller 604 controls and drives the thermoelectric cooler unit 804.

In the illustrated example, the laser module 112 also includes spacers 860 for mechanical mounting of the laser module 112 within or on the body-mounted LIO system 100-1, table-top LIO system 100-2, photocoagulation probe laser treatment system 100-3, or slit lamp device 101.

In the illustrated embodiment, the circuit board 650 is secured to a bottom surface of the housing 806 and is electrically connected to the laser diodes 916 and the external power monitor 618.

Figure 9:
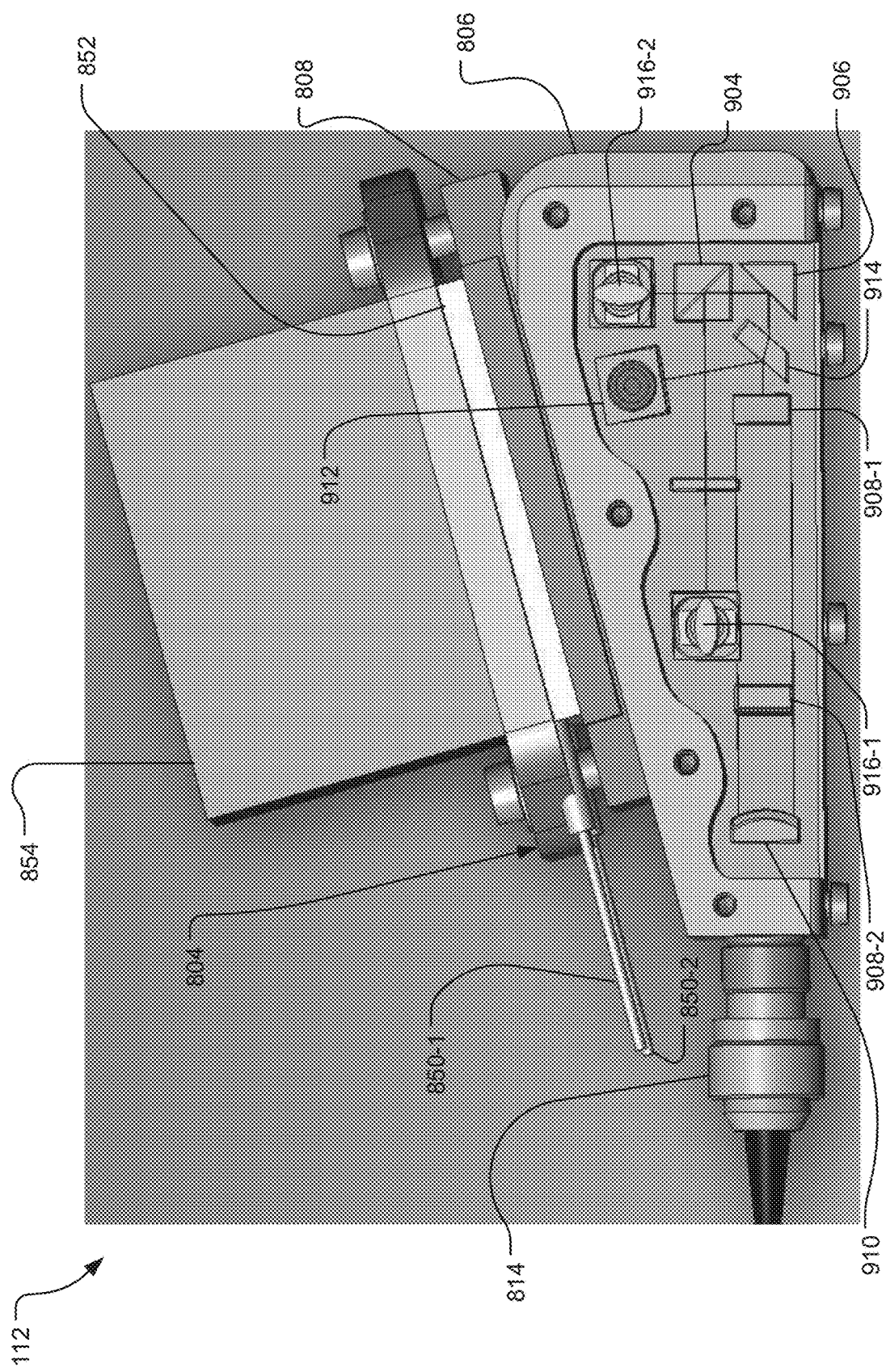
FIG. 9 is a side cutaway view of the laser module.

FIG. 9 is a to view of the laser package 112 with its lid removed to show internal components including two green laser diodes 916, a red laser diode 912, a polarization combiner 904, a fold mirror 906, a spectral combiner 914, two beam shaper elements 908 and a focusing lens 910. The laser diodes 916-1, 916-2 and 912 produce laser energy (e.g. beams) of particular wavelengths (e.g. in the wavelength range of 495-580 nm associated with visible green and yellow light for the green laser diodes 916, or the wavelength range associated with visible red light for the red laser diode 912, which produces an aiming beam). The green laser diodes 916-1, 916-2 are mounted such that they have mutually orthogonal polarizations. The laser energy produced by the green laser diodes 916-1, 916-2 are combined by the polarization combiner 904, which reflects one of the beams while transmitting the other, resulting in both propagating in the same direction. The fold mirror 906 directs the combined beam to the spectral combiner 914, which combines the beam produced by the green laser diodes 916 with the beam produced by the red laser diode 912 by reflecting one of the beams while transmitting the other based on the wavelengths of the beams, resulting in both beams propagating in the same direction. The spectral combiner 914 directs the combined beam through the shaper elements 908-1, 908-2, which form a pair of negative and positive cylindrical lenses (e.g. cylindrical telescope). The beam is further directed through the focusing lens 910 to the fiber optic cable 206 via the fiber optic connecter 814.

FIGS. 10A, 10B, 10C, 11A, 11B and 11C are exemplary wave form diagrams showing an exemplary envelope 1010 and series of micropulses 1000.

In all examples, the series of micropulses 1000 are plotted as a curve on a graph with respect to time and amplitude with an x-axis corresponding to time and a y-axis corresponding to amplitude. The curve 1002 has a higher amplitude state and a lower amplitude state represented by regions of the curves in which the curves have sustained periods of higher and lower amplitude respectively. In general, the length of the discrete higher amplitude and lower amplitude portions of the curve correspond to different time values that inform the characteristics of the envelope and the series of micropulses. In practice, the higher amplitude state corresponds to the peak power, which is the power of the delivered laser energy during each micropulse 1000.

The curve 1002 depicted with a solid line shows the series of micropulses 1000. Each micropulse 1000 includes a portion of the curve at the higher amplitude state followed by a portion of the curve at the lower amplitude state, the combined length of which indicates the micropulse period 1004. The portions of the curve at the higher amplitude state correspond to moments when laser energy is delivered to the eye, the length of which indicates the micropulse duration 1006. The portions of the curve at the lower amplitude state correspond to moments when no laser energy is delivered to the eye, the length of which indicates the micropulse interval 1008.

The dashed line represents the envelope 1010, which spans the period of time starting with the beginning of the first micropulse 1000-1 and ending at the end of the last micropulse 1000-7 of the series. The horizontal length of the envelope 1010 indicates the pulse train duration 1012, while the vertical length of the envelope corresponds to the peak power 1014 of the laser energy delivered.

Each micropulse 1000 of the series has the same period 1004, duration 1006, and interval 1008. As such, they are repeated at evenly spaced intervals across the envelope 1010.

A proportion of the micropulse duration 1006 to the micropulse period 1004 for each micropulse is referred to as the duty cycle.

In practice, the micropulse durations 1006 are in the range of 50 to 300 microseconds for periods of about 2 milliseconds, with a duty cycle ranging from 5 to 15%. The pulse train durations 1012 would range from 10 milliseconds to 1.5 seconds, with periods 1004 of any value.

Figure 10A:
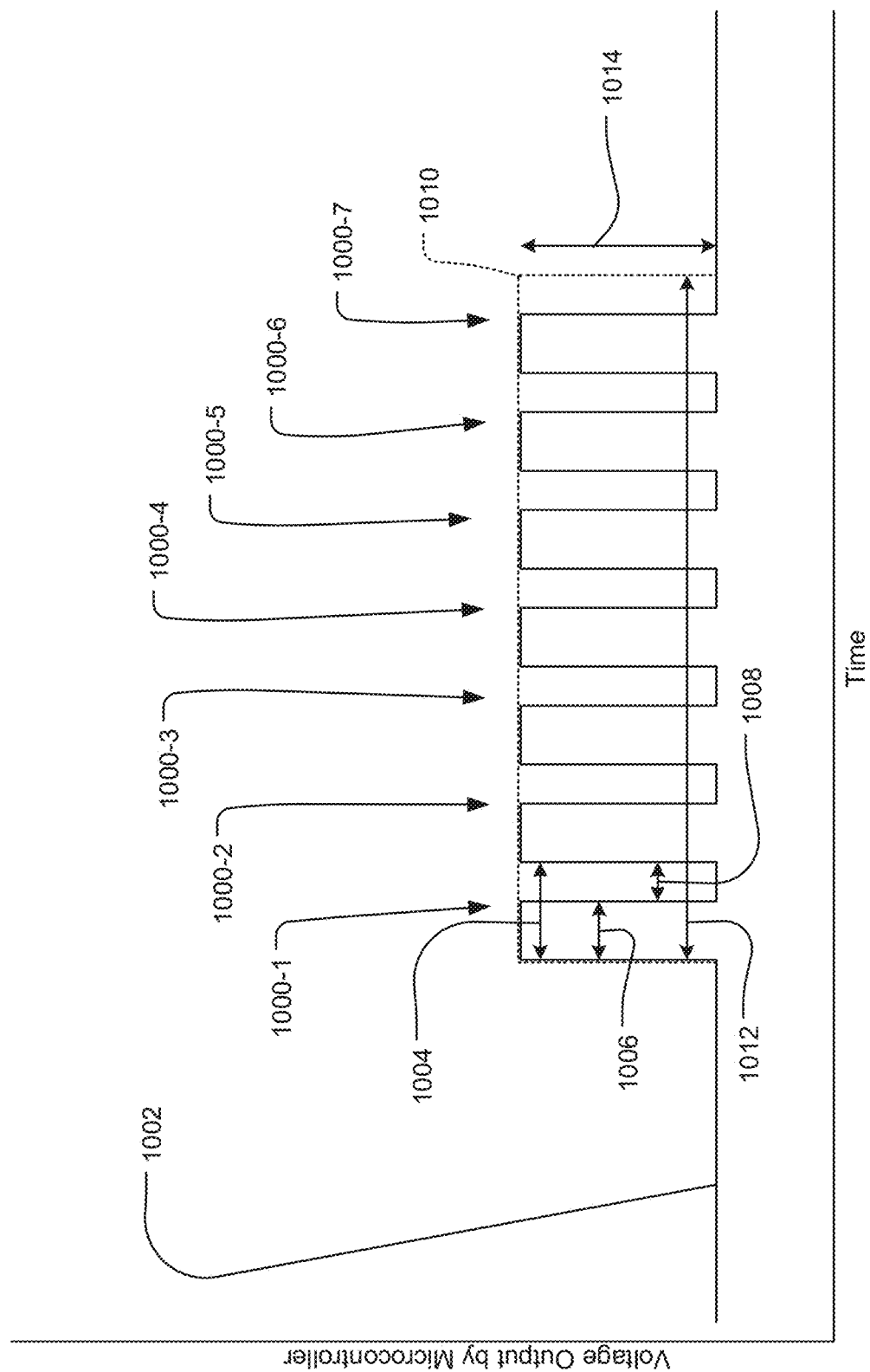
FIG. 10A is a wave form diagram showing a first exemplary envelope and series of micropulses with the micropulses shown as variations in a modulated output voltage from a microcontroller.
Figure 10B:
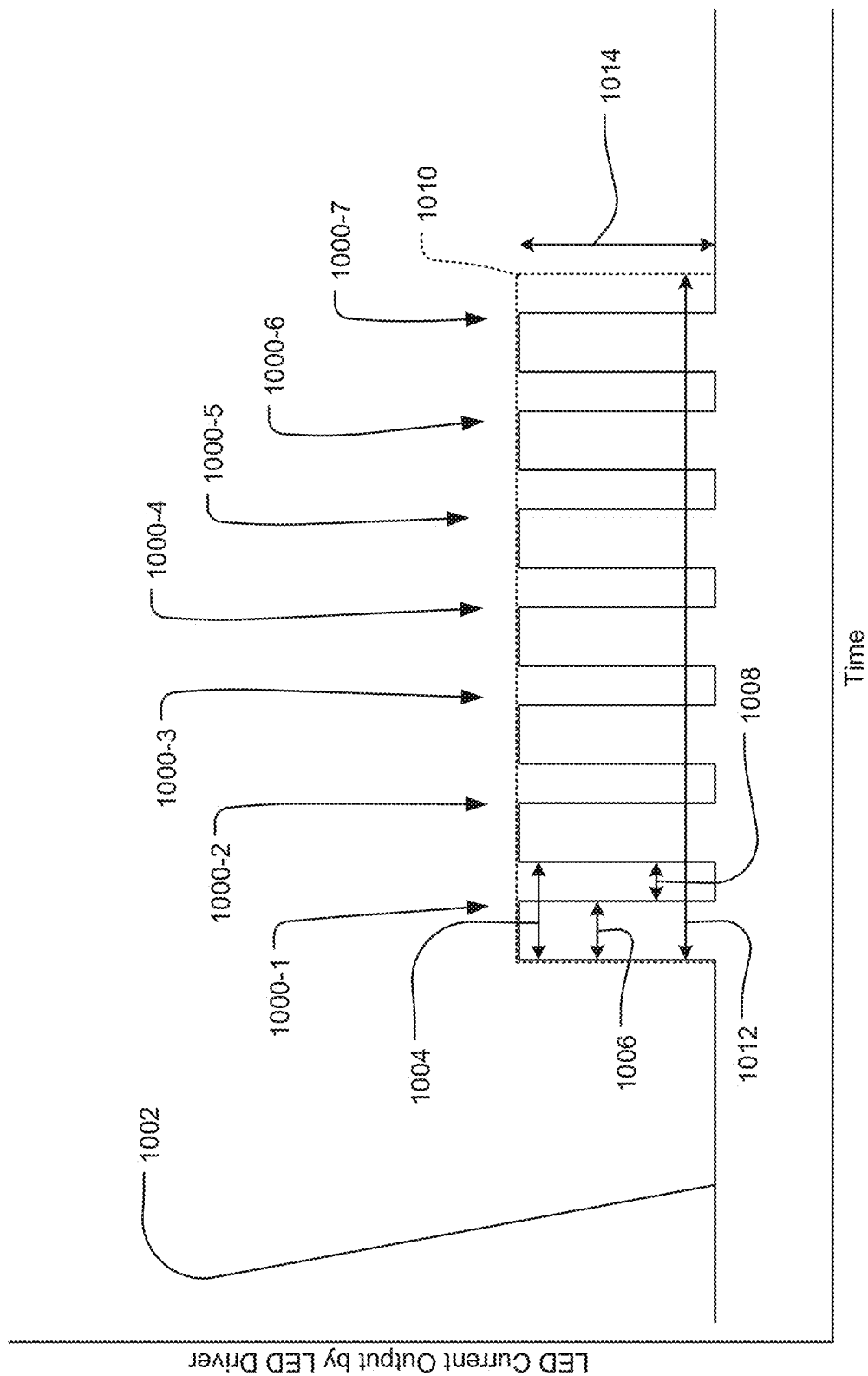
FIG. 10B is a wave form diagram showing the first exemplary envelope and micropulses as variations in a light emitting diode (LED) current from an LED driver.
Figure 10C:
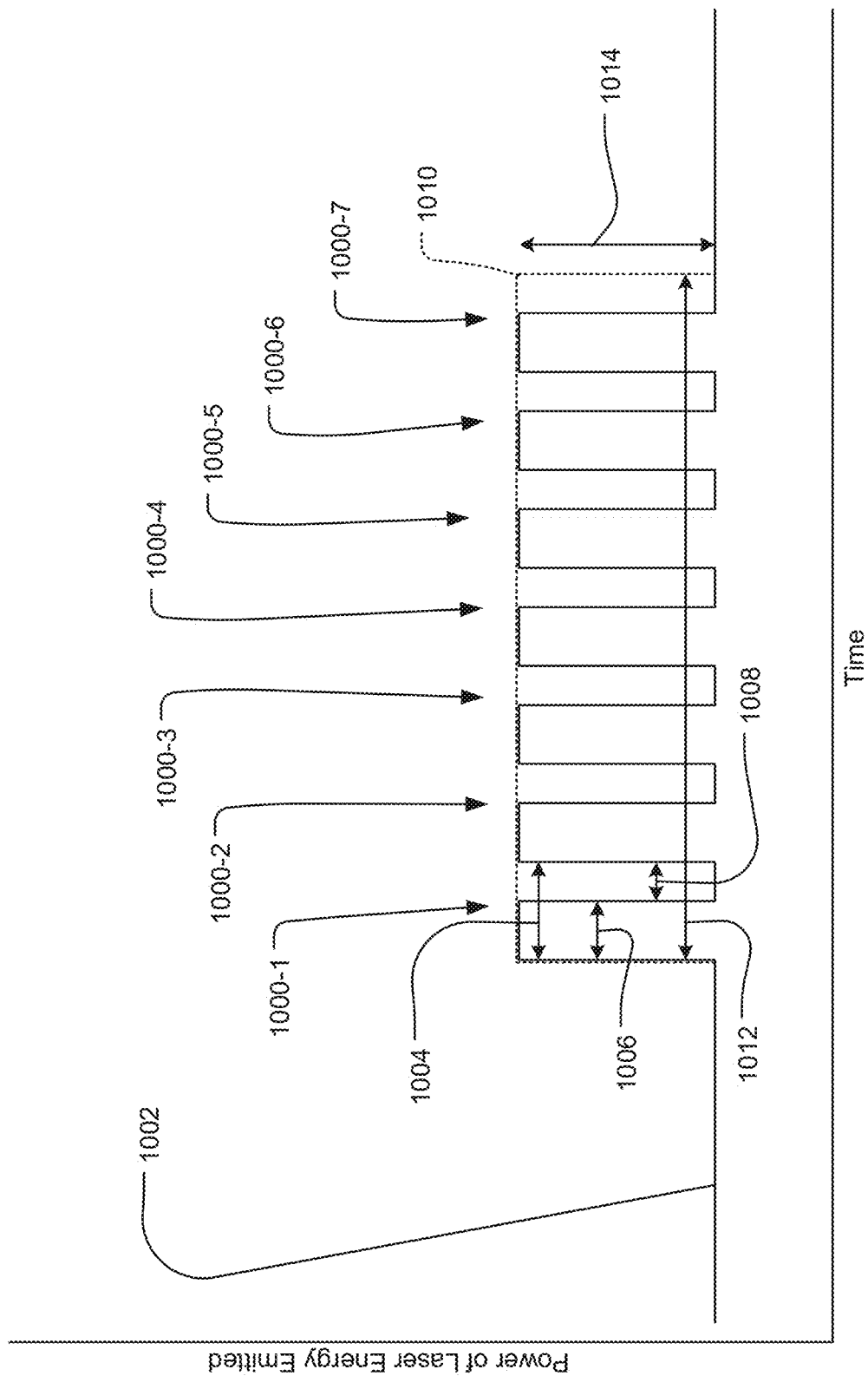
FIG. 10C is a wave form diagram showing the first exemplary envelope and micropulses as variations in power of laser energy emitted by the laser module.
Figure 11A:
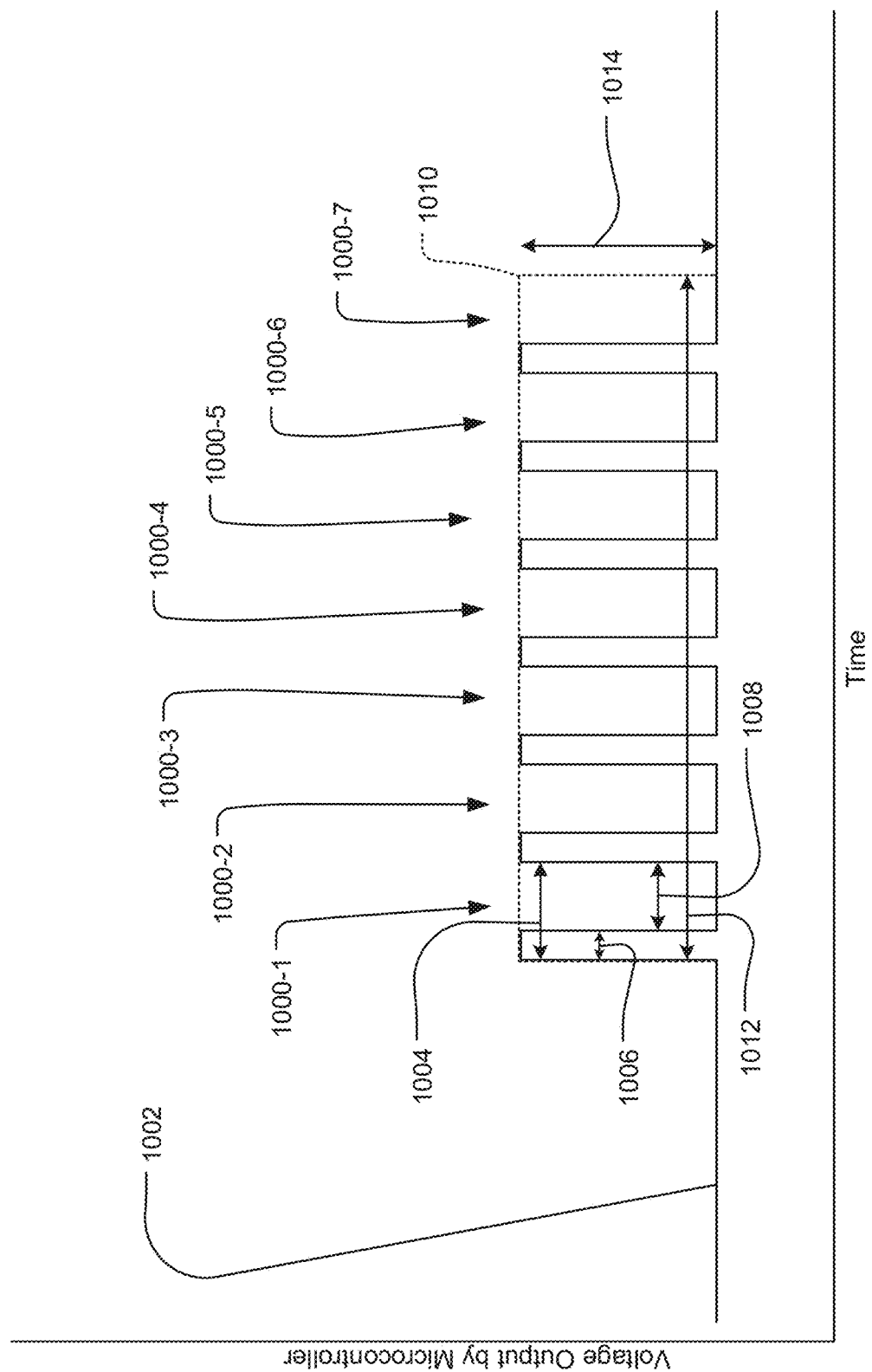
FIG. 11A is a wave form diagram showing a second exemplary envelope and series of micropulses with the micropulses shown as variations in the modulated output voltage from the microcontroller.
Figure 11B:
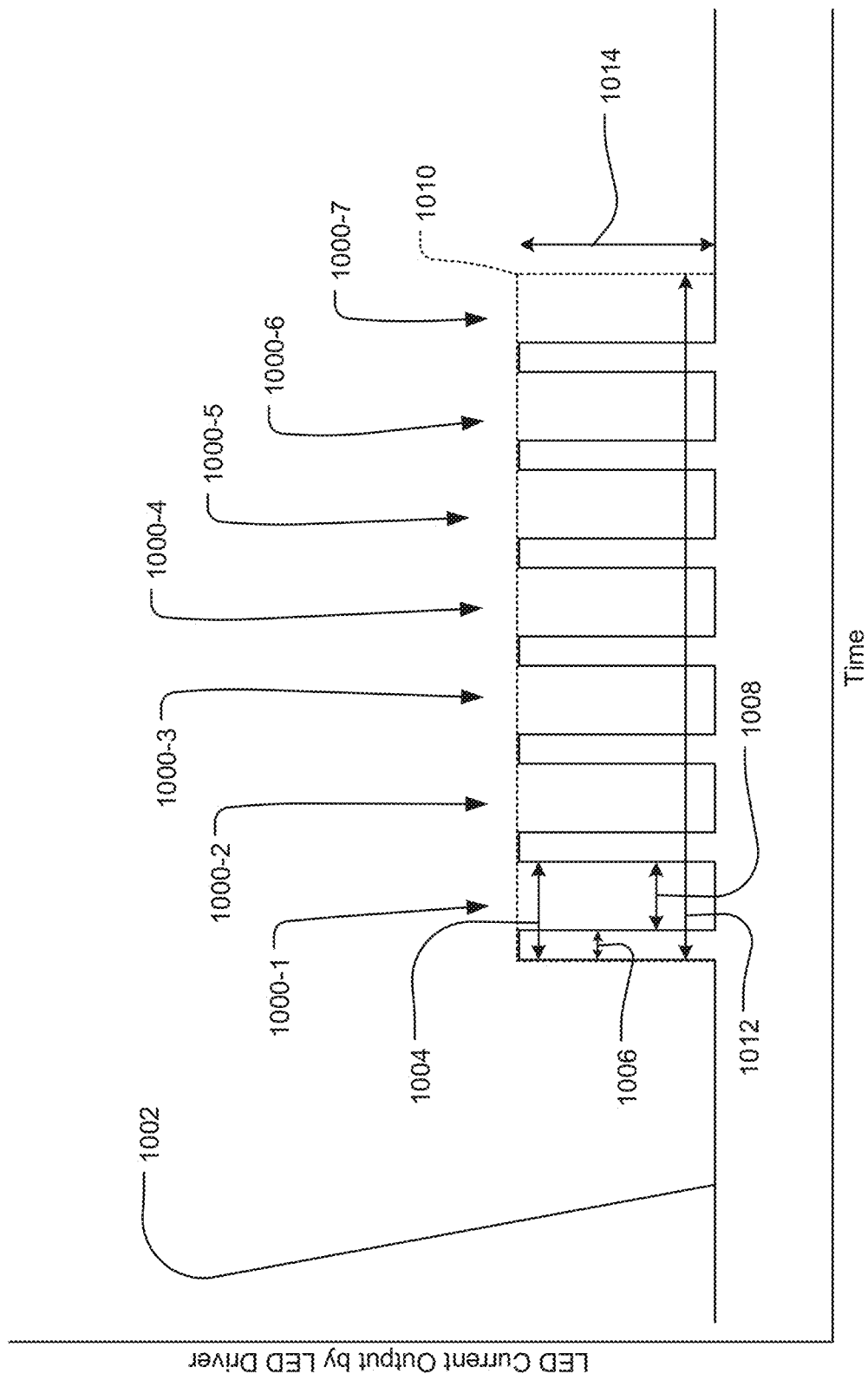
FIG. 11B is a wave form diagram showing the second exemplary envelope and micropulses as variations in the LED current from the LED driver.
Figure 11C:
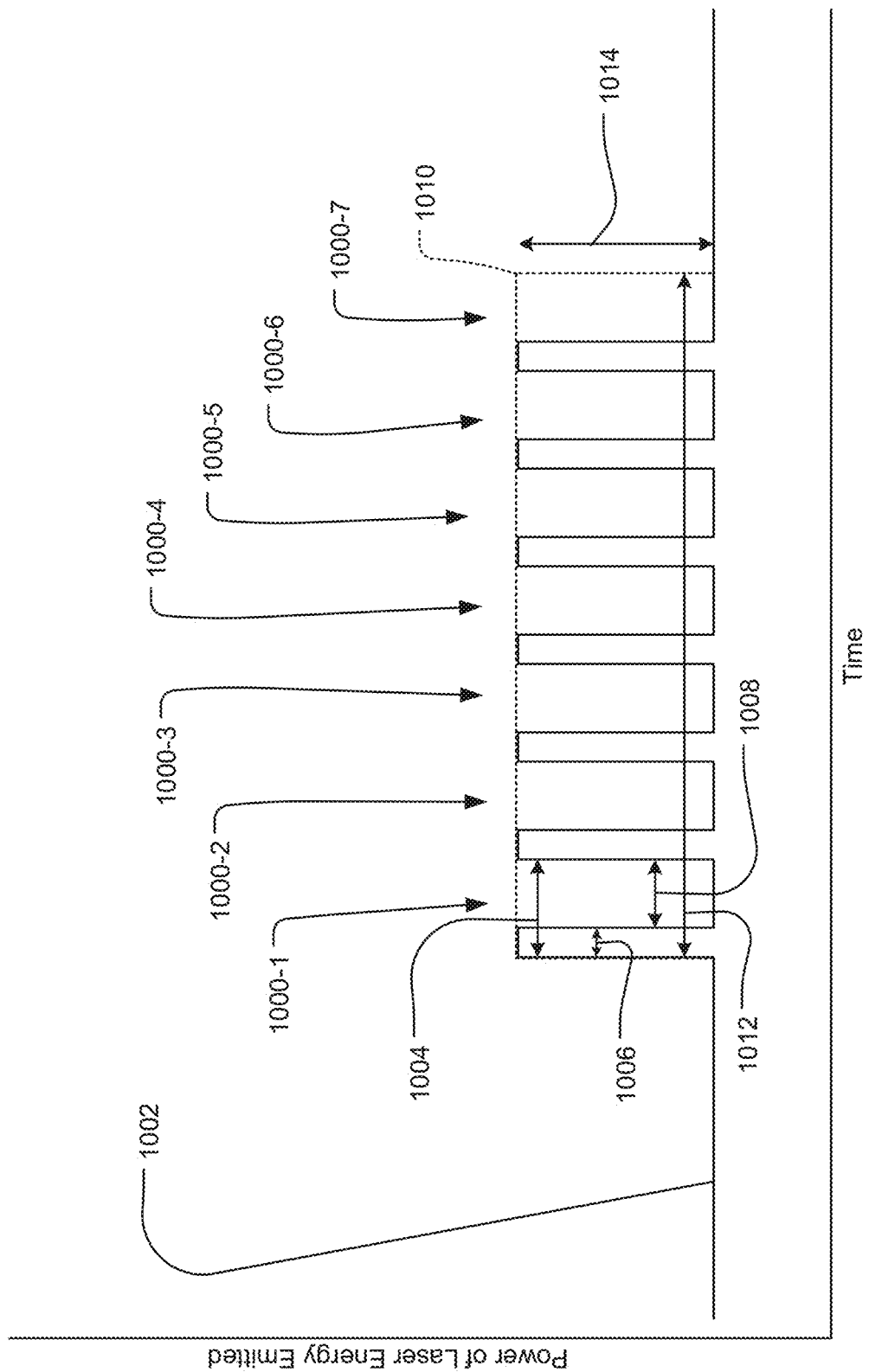
FIG. 11C is a wave form diagram showing the second exemplary envelope and micropulses as variations in the power of the laser energy emitted by the laser module.

FIGS. 10A, 10B and 10C show an exemplary wave form diagram in which the micropulse duration 1006 is longer, and the duty cycle is higher, while FIGS. 11A, 11B and 11C show an exemplary wave form diagram in which the micropulse duration 1006 is shorter, and the duty cycle is lower. In both examples, the envelope 1010 has the same horizontal and vertical width, as the amplitude 1014 and pulse train duration 1012 are the same, with only the micropulse duration 1006 and micropulse intervals 1008 varying. As a result, the average power of emitted laser energy in the example of FIGS. 10A, 10B and 10C would be higher than the average power in the example of FIGS. 11A, 11B and 11C.

More specifically, FIGS. 10A and 11A show the micropulses 1000 as variations in a modulated output voltage from the microcontroller 604 to the LED driver 614. Here, the micropulses 1000 form a binary pulse train received by the LED driver 614. The LED driver 614 outputs the LED current to the diodes 916 based on the pulse train with a higher LED current output by the LED driver 614 in response to higher voltage received from the microcontroller 604 (e.g. corresponding to the micropulse duration 1006) and a lower LED current output by the LED driver 614 in response to lower voltage received from the microcontroller 604 (e.g. corresponding to the micropulse interval 1008).

FIGS. 10B and 11B show the micropulses 1000 as variations in an LED current output by the LED driver 614 in response to the PWM signal received from the microcontroller 604 and adjusted based on the dimming signal received from the integrator 612 in the feedback process between the integrator 612 and the LED driver 614. The LED current shown in FIGS. 10B and 11B generally correspond to the PWM signal depicted in FIGS. 10A and 10B respectively in that periods of high and low LED current form a pulse train with the same or proportional characteristics (e.g. envelope, duration, pulse duration, pulse interval). The diodes 916 emit laser energy in response to receiving the higher LED current (e.g. corresponding to the micropulse duration 1006) and emit no laser energy in response to receiving the lower LED current (e.g. corresponding to the micropulse interval 1008).

FIGS. 10C and 11C show the micropulses 1000 as variations in power of laser energy emitted by the laser module 112 in response to the LED current received from the LED driver 614. The power shown in FIGS. 10C and 11C generally correspond to the LED current depicted in FIGS. 10B and 11B respectively in that periods of high and low power form a pulse train with the same or proportional characteristics (e.g. envelope, duration, pulse duration, pulse interval). The variations in power of the laser energy emitted from the pulsed laser energy delivered to the patient's eye for ophthalmic treatment.

While this invention has been particularly shown and described with references to preferred embodiments thereof, it will be understood by those skilled in the art that various changes in form and details may be made therein without departing from the scope of the invention encompassed by the appended claims.

What is claimed is:

1. A laser module for producing pulsed laser energy for an ophthalmic laser treatment system, the laser module comprising:
   one or more diodes for producing pulsed laser energy in a visible green wavelength range, wherein durations of discrete pulses of the pulsed laser energy are in a range of 50 to 300 microseconds;
   a controller for driving the one or more diodes based on parameter information;
   a power monitor that measures a power of the laser energy and outputs a detected power signal corresponding to the measured power; and
   an integrator for adjusting power of the laser energy based on a comparison of detected power signal to a predetermined a power set point based on the parameter information.

2. The laser module of claim 1, wherein the one or more diodes are configured to produce laser energy with an output power of 1 Watt.

3. The laser module of claim 1, wherein the visible green wavelength range includes wavelengths from 495 to 580 nanometers.

4. The laser module of claim 1, wherein the parameter information includes pulse envelope duration, peak power, interval, pulse duration and pulse interval.

5. The laser module of claim 1, wherein the parameter information is based on input received from a user via a user interface of the ophthalmic laser treatment system.

6. The laser module of claim 1, further comprising a light emitting diode (LED) driver for producing an LED current based on a dimming signal from the integrator, wherein the one or more diodes produce the pulsed laser energy based on the LED current from the LED driver.

7. The laser module of claim 1, wherein the ophthalmic laser treatment system is a body-mounted and/or table-top laser indirect ophthalmoscope system, a slit-lamp system, or a photocoagulation laser probe system.

8. The laser module of claim 1, wherein the laser module directs a laser current through a junction of each of the one or more diodes to produce a beam of laser energy of a particular wavelength in the visible green range, and each of the one or more diodes is configured to produce the laser energy of the particular wavelength with an output power in a range of 1-1.3 Watts.

9. The laser module of claim 8, wherein the laser module electronically pulses each of the one or more diodes in the microsecond range based on the parameter information.

10. The laser module of claim 1, further comprising an optical package, which is hermetically sealed and defines a chamber containing optical components of the laser module including the one or more diodes.

11. The laser module of claim 10, wherein the optical package comprises a lid secured over one or more surfaces of the optical package, enclosing and hermetically sealing the optical components of the laser module.

12. The laser module of claim 10, further comprising a heat sink, which transfers heat generated by the one or more diodes in the optical package.

13. The laser module of claim 10, further comprising a thermoelectric cooler unit for transferring heat generated by the one or more diodes in the optical package away from the optical package.

14. The laser module of claim 10, comprising a heat sink and a thermoelectric cooler unit, wherein the thermoelectric cooler unit comprises a cooling plate with thermocouples, an electric current moves through the thermocouples causing one side of the cooling plate to be cooled and another side of the cooling plate to be heated, the heat sink of the laser module transferring heat from the optical package to the cooled side of the cooling plate, and a heat sink of the thermoelectric cooler unit, which is in contact with the heated side of the cooling plate, dissipates heat from the heated side of the cooling plate.

15. The laser module of claim 10, wherein the optical package comprises a fiber optic connector for coupling the laser energy through a fiber optic cable.

16. A method for producing pulsed laser energy for an ophthalmic laser treatment system, the laser module comprising:
receiving parameter information; and
one or more diodes producing pulsed laser energy in a visible green wavelength range based on the parameter information, wherein durations of discrete pulses of the pulsed laser energy are in a range of 50 to 300 microseconds;
measuring the power of the laser energy and outputting a detected power signal corresponding to the measured power;
adjusting power of the laser energy based on a comparison of detected power signal to a predetermined power set point based on the parameter information.

17. The method of claim 16, further comprising the one or more diodes producing the laser energy with an output power of 1 Watt.

18. The method of claim 16, wherein the visible green wavelength range includes wavelengths from 495 to 580 nanometers.

19. The method of claim 16, wherein the parameter information includes pulse envelope duration, peak power, interval, pulse duration and pulse interval.

20. The method of claim 16, further comprising generating the parameter information based on input received from a user via a user interface of the ophthalmic laser treatment system.

21. The method of claim 16, further comprising modulating an output voltage by a controller of the laser module based on the parameter information, producing a light emitting diode (LED) current by an LED driver based on a modulated output voltage, wherein the one or more diodes produce the pulsed laser energy based on the LED current.

22. The method of claim 16, wherein the ophthalmic laser treatment system is a body-mounted and/or table-top laser indirect ophthalmoscope system, a slit-lamp system, or a photocoagulation laser probe system.

23. A system for delivering pulsed laser energy to an eye of a patient, the system comprising:
a control module for setting parameters for the delivered pulsed laser energy based on received parameter information and sending control signals based on the parameters;
a laser module for delivering the pulsed laser energy based on the control signals, wherein the laser module comprises one or more diodes for producing the pulsed laser energy in a visible green wavelength range, and durations of discrete pulses of the pulsed laser energy are in a range of 50 to 300 microseconds;
an optical package, which is hermetically sealed and defines a chamber containing optical components of the laser module including the one or more diodes and has a lid secured over one or more surfaces of the optical package, enclosing and hermetically sealing the optical components of the laser module; and
a thermoelectric cooler unit for transferring heat generated by the one or more diodes in the optical package away from the optical package.

* * * * *